US00PP29203P3

(12) United States Plant Patent
Park

(10) Patent No.: US PP29,203 P3
(45) Date of Patent: Apr. 3, 2018

(54) ***COREOPSIS* PLANT NAMED 'URITW01'**

(50) Latin Name: ***Coreopsis rosea*×*Coreopsis verticillata***
Varietal Denomination: URITW01

(71) Applicant: Uriseed Institute, Icheon-si (KR)

(72) Inventor: Kong Young Park, Icheon-si (KR)

(73) Assignee: URISEED INSTITUTE, Icheon-si (KR)

( * ) Notice: Subject to any disclaimer, the term of this patent is extended or adjusted under 35 U.S.C. 154(b) by 15 days.

(21) Appl. No.: 14/999,128

(22) Filed: Mar. 31, 2016

(65) Prior Publication Data

US 2017/0049029 P1 Feb. 16, 2017

(30) Foreign Application Priority Data

Aug. 14, 2015 (EM) ..... 20151905

(51) Int. Cl.
*A01H 5/02* (2006.01)

(52) U.S. Cl.
USPC ..... Plt./417

(58) Field of Classification Search
USPC ..... Plt./417
CPC ..... A01H 5/025; A01H 5/02; A01H 5/00
See application file for complete search history.

(56) References Cited

U.S. PATENT DOCUMENTS

PP15,455 P3 * 12/2004 Faria ..... Plt./417

OTHER PUBLICATIONS

Jala Morphological Change Due to Effects of Acute Gamma Ray on Wishbone Flower (*Torenia fourmieri*) In Vitro, 2011 International Transaction Journal of Engineering, Management, & Applied Sciences & Technologies, vol. 2 No. 4, 375-383.*

Horticulture Week Plantarium 2015 new plants announced, retrieved on Jun. 26, 2017, retrieved from the Internet at <http://www.hortweek.com/plantarium-2015-new-plants-announced/ornamentals/article/1359559> pp. 1 and 7.*

New Plants and Flower, Three Korean *Coreopsis* varieties launched in Europe, retrieved on Jun. 26, 2017, retrieved from the Internet at <http://www.newplantsandflowers.com/three-korean-coreopsis-varieties-launched-in-europe/> 2 pp.*

Park et al Development of a new *Coreopsis* variety 'Uridream Pink' by gamma-ray irradiation, Kor. J. Hort. Sci. Technol. 32(6):906-911, 2014.*

Park et al English translation 2017 pp. 1-15.*

* cited by examiner

*Primary Examiner* — June Hwu
(74) *Attorney, Agent, or Firm* — Penny J. Aguirre

(57) ABSTRACT

A new cultivar of hybrid *Coreopsis* plant named, 'URITW01', that is characterized by its dwarf plant habit, its small inflorescences with ray florets that are dark crimson red in color, and its involucral bracts that are small in size and oblong to ovate in shape.

2 Drawing Sheets

Botanical classification: *Coreopsis rose*×*Coreopsis verticillata.*

Variety denomination: 'URITW01'.

CROSS REFERENCE TO RELATED APPLICATIONS

This application is co-pending with U.S. Plant Patent Applications filed for plants derived from the same breeding program that are entitled *Coreopsis* Plant Named 'URITW02' (U.S. Plant patent application Ser. No. 14/999,136) and *Coreopsis* Plant Named 'URITW03' (U.S. Plant patent application Ser. No. 14/999,135).

BACKGROUND OF THE INVENTION

The present invention relates to a new and distinct cultivar of *Coreopsis* plant, botanically of hybrid origin and known as *Coreopsis* 'URITW01' and will be referred to hereinafter by its cultivar name, 'URITW01'. The new cultivar of *Coreopsis* is an herbaceous perennial grown for landscape and container use.

The new invention arose from an ongoing controlled breeding program in Icheon-si, Korea. The objective of the breeding program is to develop hybrid cultivars of *Coreopsis* with unique flower colors and dwarf plant habit.

The new cultivar arose as a mutation using gamma radiation of un-rooted cuttings of unknown, unnamed proprietary plants from the Inventor's breeding program in January of 2010. 'Limerock Ruby' (U.S. Plant Pat. No. 15,455) and addition cultivars were initially used in the breeding program in prior years to obtain initial primary mutations and subsequent rounds of gamma radiation were preformed on proprietary seedlings until. 'URITW01' was selected in September 2010 as a single unique plant amongst the resulting seedlings.

Asexual propagation of the new cultivar was first accomplished by stem cuttings by the Inventor in Icheon-si, Korea in September of 2010. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'URITW01' as unique cultivar of *Coreopsis*.

1. 'URITW01' exhibits a dwarf plant habit.
2. 'URITW01' exhibits small inflorescences with ray florets that are dark crimson red in color.
3. 'URITW01' exhibits involucral bracts that are small in size and oblong to ovate in shape.

'URITW01' can be compared to 'URITW02', 'URITW03' and 'Limerock Ruby'. 'URITW02' and 'URITW03' are similar to 'URIBL01' in having a dwarf plant habit. 'URITW02' differs from 'URIBL01' in having inflorescences with ray florets that are pink in color. 'URITW03' differs from 'URITW01' in having inflorescences with ray florets that are lighter red in color. 'Limerock Ruby' is similar to 'URITW01' in having flowers that are crimson red in color. 'Limerock Ruby' differs from 'URITW01' in having a plant height that is 50% taller, in having a wider plant spread, and in having inflorescences that larger in size.

BRIEF DESCRIPTION OF THE DRAWINGS

The accompanying colored photographs illustrate the overall appearance and distinct characteristics of the new *Coreopsis*. The photographs were taken of a 3 month-old plant of 'URITW01' as grown outdoors in a 13-cm container in Boskoop, The Netherlands.

The photograph in FIG. 1 provides a side view of a plant of 'URITW01' in bloom.

Figure 1:
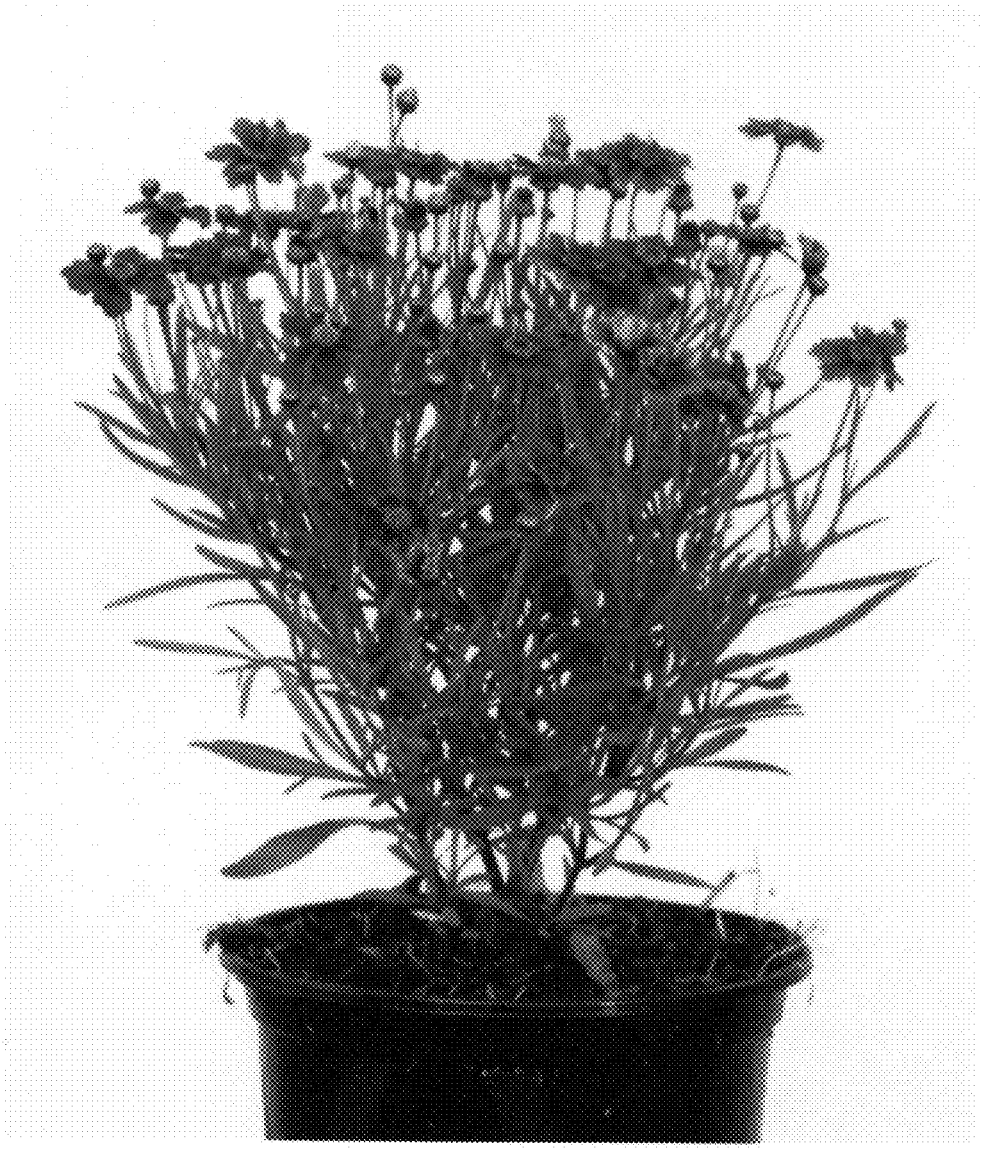
Figure 2:
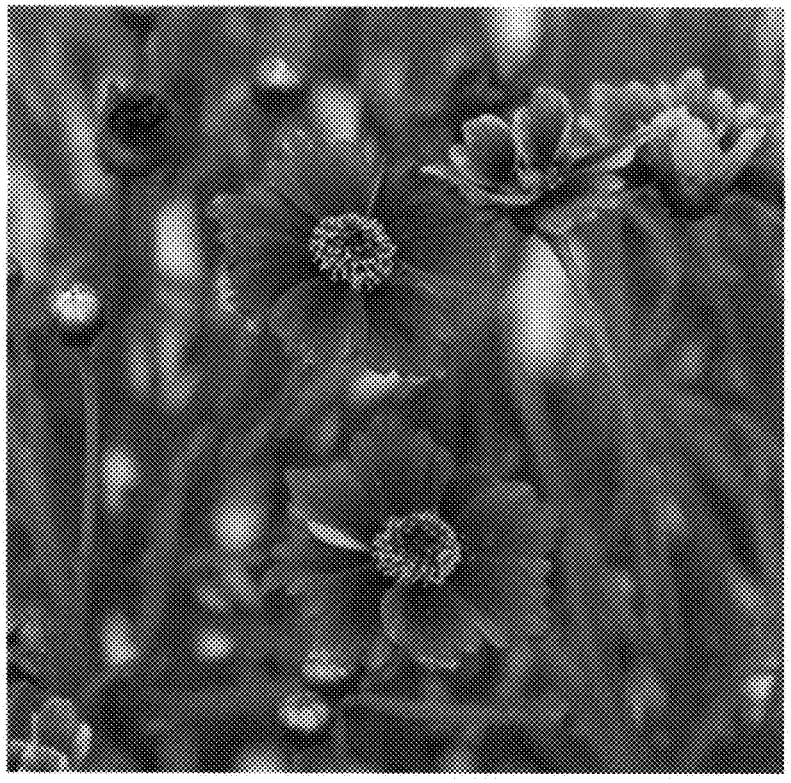

The photograph in FIG. 2 provides a close-up view of the inflorescences of 'URITW01'.

Figure 3:
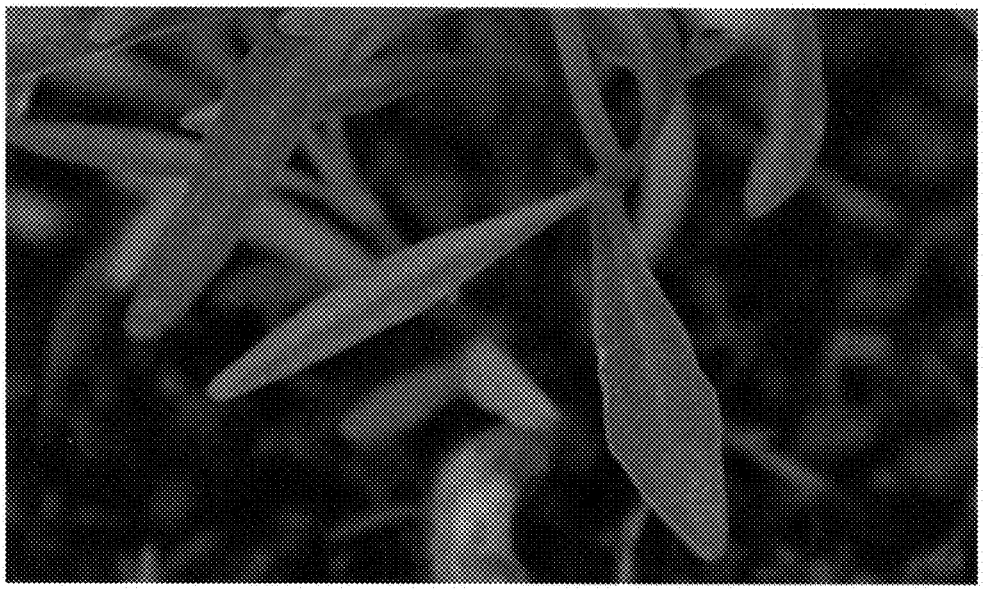

The photograph in FIG. 3 provides a close-up view of the foliage of 'URITW01'.

The colors in the photograph may differ slightly from the color values cited in the detailed botanical description, which accurately describe the colors of the new *Coreopsis*.

DETAILED BOTANICAL DESCRIPTION

The following is a detailed description of 3 month-old plants of the new cultivar as grown outdoors in 13-cm containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early summer to late summer in The Netherlands.

*Plant type*.—Herbaceous perennial.

*Plant habit*.—Dwarf and upright.

*Height and spread*.—An average of 19.8 cm in height and 19.6 cm in width.

*Cold hardiness*.—At least to U.S.D.A Zone 4.

*Diseases and pests*.—No susceptibility or resistance to diseases or pests has been observed.

*Root description*.—Fibrous when young, becoming fleshy with age, 162D in color.

*Propagation*.—Stem cuttings.

*Root development*.—An average of 10 days for root initiation and about 5 weeks to produce a young rooted plant in a 10-cm container.

*Growth rate*.—Moderate.

Stem description:

*Shape*.—Oval.

*Stem color*.—143B.

*Stem size*.—An average of 6.5 cm in length (excluding inflorescence) and 1.75 mm in diameter.

*Stem surface*.—Glabrous and glossy.

*Stem aspect*.—Upright and moderately outward.

*Stem strength*.—Strong.

*Branching habit*.—Well-branched, an average of 27 lateral branches.

*Internode length*.—An average of 2.2 cm.

Foliage description:

*Leaf type*.—Single.

*Leaf division*.—Simple.

*Leaf margins*.—Entire.

*Leaf size*.—An average of 5 cm in length and 4 mm in width.

*Leaf shape*.—Narrow lanceolate.

*Leaf base*.—Narrow cuneate.

*Leaf apex*.—Acute.

*Leaf venation*.—Pinnate, color; upper surface 143B and lower surface 144A.

*Leaf attachment*.—Sessile.

*Leaf arrangement*.—Opposite.

*Leaf surface*.—Both surfaces dull and glabrous.

*Leaf color*.—Young upper surface; 144A, young lower surface; 143C, mature upper surface 143C, mature lower surface 143A.

*Leaf number*.—An average of 6 leaves (3 pairs) per stem.

Inflorescence description:

*Inflorescence type*.—Terminal capitulate, with a single row of ray florets surrounding disk florets in the center.

*Lastingness of inflorescence*.—An average of 3 weeks, self-cleaning.

*Fragrance*.—Moderate to faint, of musk and straw.

*Quantity of inflorescences*.—An average of 2 per lateral branch.

*Inflorescence size*.—An average of 2.3 cm in diameter, 6 mm in height, disk portion an average of 6 mm in diameter.

*Inflorescence buds*.—An average of 4 mm in depth and in diameter, globular in shape, color; 147A with apex 153A and longitudinal stripes 178B.

*Peduncle*.—Primary; an average of 5.0 cm in length and 1 mm in width, held straight upright, secondary; an average of 4.7 cm in length and 1 mm in width, held at an average angle of 25° to primary peduncle, slightly glossy and glabrous on all surfaces and 144B in color.

Involucral bracts:

*Bract arrangement*.—Rotate, placed in two separate rows.

*Bract number*.—An average of 8 bracts in the inner row and 6 bracts in the outer row.

*Bract size*.—Outer bracts; an average of 2 mm in length and 1.5 mm in width, inner bracts; an average of 5 mm in length and 3 mm in width.

*Bract color*.—Inner bracts; 153D heavily suffused with N25C with base 146A, outer bracts; 143A.

*Bract texture*.—Glabrous and slightly glossy on outer and inner surfaces of outer and inner bracts.

*Bract apex*.—Outer bracts; obtuse and inner bracts; acute.

*Bract base*.—Broadly cuneate on inner and outer bracts.

*Bract margins*.—Entire.

*Bract shape*.—Outer bracts; narrow ovate to oblong, inner bracts; ovate.

Ray florets (sterile):

*Number*.—An average of 8 arranged primarily in one row.

*Shape*.—Obovate.

*Size*.—An average of 1.0 cm in length and 8 mm in width.

*Apex*.—Irregularly lobed with an average of 3 bluntly acute lobes, center lobe is about 1.5 mm longer than the lateral lobes.

*Base*.—Rounded.

*Margins*.—Entire with apex lobed.

*Aspect*.—Held horizontal to slightly upward.

*Texture*.—Glabrous on both surfaces, upper surface; velvety lower surface; moderately carinate.

*Color*.—Upper surface when opening; 59A with apex 68B, lower surface when opening; 182D, upper surface when fully open; 59A with apex 60C, lower surface when fully open; 185D, color not fading.

Disc florets (perfect):

*Shape*.—Tubular, spirally arranged on disc.

*Apex*.—Acute.

*Base*.—Lower 75% fused into tube.

*Number*.—About 50.

*Size*.—An average of 4 mm in length and 1 mm in width at the apex and 0.4 mm in width at the base.

*Color*.—En masse; 178C, corolla; base of tube is 6D to 6C in color, flared portion is 178C.

*Receptacle*.—An average of 1.0 mm in diameter and depth, 143B in color.

Reproductive organs:

*Presence*.—Disc florets are perfect, ray florets are sterile.

*Gynoecium*.—1 pistil, an average of 2 mm in length, style; an average of 1.5 mm in length and 16A in color, stigma is decurrent and 21A to 21B in color, ovary is 150D in color.

*Androecium*.—5 stamens, anther; basifixed and linear in shape, an average of 1 mm in length and 203D in color, pollen is low in quantity and 17B in color.

*Fruit/seed*.—No fruit or seed development was observed to date.

It is claimed:

1. A new and distinct cultivar of *Coreopsis* plant named 'URITW01' as herein illustrated and described.

* * * * *